United States Patent
Huang et al.

(10) Patent No.: US 11,304,775 B2
(45) Date of Patent: Apr. 19, 2022

(54) METHOD FOR AUTOMATEDLY ALIGNING A STAND FOR A MICROSCOPE, STAND FOR A MICROSCOPE AND MICROSCOPE ASSEMBLY

(71) Applicant: LEICA INSTRUMENTS (SINGAPORE) PTE. LTD., Singapore (SG)

(72) Inventors: Jason Huang, Singapore (SG); Chin Yi Liaw, Singapore (SG)

(73) Assignee: LEICA INSTRUMENTS (SINGAPORE) PTE. LTD., Singapore (SG)

(*) Notice: Subject to any disclaimer, the term of this patent is extended or adjusted under 35 U.S.C. 154(b) by 639 days.

(21) Appl. No.: 16/250,223

(22) Filed: Jan. 17, 2019

(65) Prior Publication Data
US 2019/0223973 A1 Jul. 25, 2019

(30) Foreign Application Priority Data
Jan. 19, 2018 (EP) .................. 18152619

(51) Int. Cl.
*A61B 90/25* (2016.01)
*G05D 3/12* (2006.01)
(Continued)

(52) U.S. Cl.
CPC .............. *A61B 90/25* (2016.02); *G02B 7/001* (2013.01); *G02B 21/0012* (2013.01); *G05D 3/12* (2013.01);
(Continued)

(58) Field of Classification Search
CPC .... G02B 21/241; G02B 21/242; G02B 21/26; G02B 21/16; G02B 21/244; G02B 21/24;
(Continued)

(56) References Cited

U.S. PATENT DOCUMENTS

| 2011/0234977 A1* | 9/2011 | Verdooner | ............ A61B 3/145 351/207 |
|---|---|---|---|
| 2015/0346473 A1 | 12/2015 | Ernsperger et al. | |
| 2017/0176704 A1 | 6/2017 | Hirose et al. | |

FOREIGN PATENT DOCUMENTS

| DE | 102009037018 A1 | 2/2011 |
|---|---|---|
| JP | 2004-317970 A | 11/2004 |

(Continued)

OTHER PUBLICATIONS

"OPMI Pentero C Software Release 2.20/2.21," Carl Zeiss Surgical GmbH, 2009, issue 4.2, pp. 1-409.

*Primary Examiner* — Collin X Beatty
*Assistant Examiner* — Grant A Gagnon
(74) *Attorney, Agent, or Firm* — Hodgson Russ LLP

(57) ABSTRACT

The invention relates to a method for automatedly aligning a stand (12) for a microscope (14), wherein the stand (12) for the microscope (14) comprises controllable positioning means (16) for positioning the microscope (14) and controllable orienting means (18) for orienting the microscope (14). The method comprises defining a target point (24) to be observed by the microscope (14), wherein the target point (24) is located within a coordinate range accessible by the stand (12), stabilizing the microscope (14) at a user determined position in an automated manner by means of the controllable positioning means (16) of the stand, and adjusting an orientation of the microscope (14) at the user determined position to the target point (24) in an automated manner using the controllable orienting means (18) of the stand. The invention further relates to a stand, a microscope assembly (10), a control unit, a computer program and a computer-readable data storage.

16 Claims, 10 Drawing Sheets

(51) Int. Cl.
　　*G02B 21/00*　　　(2006.01)
　　*G02B 21/24*　　　(2006.01)
　　*G02B 7/00*　　　(2021.01)
　　*A61B 90/00*　　　(2016.01)

(52) U.S. Cl.
　　CPC .............. *A61B 90/36* (2016.02); *G02B 21/24* (2013.01); *G02B 21/241* (2013.01)

(58) Field of Classification Search
　　CPC .. G02B 21/367; G02B 21/006; G02B 21/245; G02B 21/0088; G02B 21/06; G02B 21/365; G02B 21/002; G02B 21/02; G02B 21/248; G02B 21/34; G02B 21/0016; G02B 21/0076; G02B 21/008; G02B 21/361; G02B 21/0032; G02B 21/08; G02B 21/247; G02B 21/362; G02B 7/28; G02B 21/00; G02B 21/0008; G02B 21/0012; G02B 21/0048; G02B 21/0052; G02B 21/0064; G02B 21/082; G02B 21/18; G02B 21/22; G02B 27/068; G02B 7/04; G02B 7/09; G02B 21/0024; G02B 21/0028; G02B 21/0036; G02B 21/0068; G02B 21/0072; G02B 21/0084; G02B 21/0096; G02B 21/025; G02B 21/086; G02B 21/088; G02B 21/12; G02B 21/125; G02B 21/32; G02B 21/33; G02B 21/368; G02B 2207/114; G02B 23/18; G02B 26/005; G02B 26/06; G02B 26/0816; G02B 27/0012; G02B 27/0025; G02B 27/0075; G02B 27/1006; G02B 27/1066; G02B 27/141; G02B 27/145; G02B 30/34; G02B 30/36; G02B 3/14; G02B 5/1885; G02B 5/3083; G02B 7/006; G02B 7/028; G02B 7/06; G02B 7/08; G02B 7/38; A61B 2090/0813; A61B 3/14; A61B 90/20; A61B 90/25; A61B 90/36; A61B 90/50; G05D 3/12
　　USPC ......................................................... 359/383
　　See application file for complete search history.

(56) References Cited

FOREIGN PATENT DOCUMENTS

JP　　2005-010665 A　　1/2005
WO　　2011116812 A1　　9/2011

* cited by examiner

METHOD FOR AUTOMATEDLY ALIGNING A STAND FOR A MICROSCOPE, STAND FOR A MICROSCOPE AND MICROSCOPE ASSEMBLY

CROSS REFERENCE TO RELATED APPLICATIONS

This application claims priority of European patent application number 18152619.5 filed Jan. 19, 2018, the entire disclosure of which is incorporated by reference herein.

FIELD OF THE INVENTION

The present invention relates to a method for automatedly aligning a stand for a microscope, a control unit for a stand for a microscope, a stand for a microscope, a microscope assembly, a computer program and a computer-readable data storage. Thus, the invention is in particular related to the field of stands for microscopes, especially for operating microscopes, i.e. surgical microscopes.

BACKGROUND OF THE INVENTION

Typical stands for surgical microscopes may provide a user of the microscope, such as a surgeon, with a large number of degrees of freedom to move the microscope with the respect to an examined object, which is to be observed by means of the microscope and to mechanically balance the microscope. For instance, the stand supporting the microscope may provide three translational degrees of freedom and also three rotatory degrees of freedom for positioning and aligning the microscope at a desired position and in a desired orientation with respect to the object. This allows in general a good accessibility and/or observability of the region of interest of the object, which is to be observed by the user of the microscope, and allows bringing the microscope to a suitable position and orientation for focusing the microscope to the region of interest.

However, when the microscope is moved by the user to a different position and/or orientation with respect to the object, typically the focusing to the region of interest is lost. Thus, the user may be required after moving the microscope to change the orientation and/or to re-align the microscope for obtaining again a suitable view on the region of interest. In particular when observing the region of interest with a high optical magnification, it might be difficult for the user to find again the region of interest and to re-align the microscope to be focused again to the desired region of interest. This may even require reducing the optical magnification for obtaining a larger field of view to be able to find again the desired region of interest, and after finding it, to readjust the optical magnification and the focusing parameter of the microscope. In any case, whenever the microscope is moved by the user to a different position and/or orientation with respect to the object, typically an effortful and/or time-consuming procedure of realignment is necessary to refocus the microscope to the desired region of interest. In particular in the course of time critical surgeries, a loss of time due to the necessity of realigning the microscope may cause severe disadvantages.

Conventional stands and methods may allow an automated realignment of the microscope to the previously set and saved position and orientation, after the microscope was moved away from this position and/or orientation, allowing the user a facilitated return to the previously chosen field of view. However, such methods do not allow the user to relocate the microscope to a different, preferred position and/or orientation, which may be for instance ergonomically better suited for the user, and to obtain an automated realignment of the microscope to the region of interest at the new position. Furthermore, such an automatic repositioning and/or realignment does not provide any assistance to the user when the user desires to observe the region of interest under a different view angle. Instead, this technique would only bring back the microscope to the previously chosen (and saved) setting with respect to the region of interest.

SUMMARY OF THE INVENTION

It is, thus, the objective technical problem of the invention to provide a method for automatedly aligning a stand for a microscope and a stand for a microscope, which overcome these disadvantages of the techniques known in prior art.

This problem is solved by a method, a stand for a microscope, a microscope assembly, a control unit, a computer program and a computer-readable data storage having the features of the respective independent claims. Preferred embodiments are subject-matter of the dependent claims and the following description.

In one aspect the invention relates to a method for automatedly aligning a stand for a microscope, wherein the stand for the microscope comprises controllable positioning means for positioning the microscope and controllable orienting means for orienting the microscope. The method comprises defining a target point to be observed by the microscope, wherein the target point is located within a coordinate range accessible by the stand (step a). Further, the method comprises stabilizing the microscope at a user determined position in an automated manner by means of the controllable positioning means of the stand (step b). Moreover, the method comprises adjusting an orientation of the microscope at the user determined position to the defined target point in an automated manner using the controllable orienting means of the stand (step c).

In another aspect the invention relates to a stand for a microscope for automatedly aligning the microscope to a target point. The stand comprises controllable positioning means for positioning the microscope with respect to an object to be observed with the microscope, controllable orienting means for orienting the microscope with respect to the object, and a control unit. The control unit is configured to define a target point to be observed by the microscope, wherein the target point is located within a coordinate range accessible by the stand (step a), to stabilize the microscope at a user determined position in an automated manner by means of the controllable positioning means of the stand (step b) and to adjust (step c) an orientation of the microscope at the user determined position to the defined target point in an automated manner using the controllable orienting means of the stand.

In another aspect the invention relates to a microscope assembly comprising a stand according to the invention and a microscope attached to the stand.

In another aspect the invention relates to a control unit for a stand for a microscope and optionally for a microscope, which is configured to cause a stand for a microscope carrying out a method according to the invention.

In another aspect the invention relates to a computer program, which is configured to cause a stand for a microscope and optionally a microscope to carry out a method according to the invention, when carried out by a control unit for the stand.

In another aspect the invention relates to computer-readable data storage having a computer program according to the invention stored thereon.

The microscope preferably may be an operating microscope, which is a surgical microscope. The stand for the microscope is preferably a mechanical construction for supporting the microscope and allowing a user to move the microscope within a given range to change the orientation and/or positioning of the microscope with respect to the object. The stand is preferably configured to stabilize the microscope, such that the microscope is preferably not moving if not actively moved by the user and/or if not repositioned and/or reoriented by the stand in an automated manner. Preferably, the stand allows moving and/or turning the microscope with respect to three translational degrees of freedom and/or three rotatory degrees of freedom. For instance, the stand may comprise several linkages, which each allow the stand and/or microscope to be moved with respect to one or more spatial degrees of freedom. Preferably, all linkages together allow the microscope to be moved and/or turned with respect to the three translational degrees of freedom and/or the three rotatory degrees of freedom. In order to stabilize the microscope, the microscope and/or the stand are optionally mechanically balanced and/or blocked in their movement with respect to the linkages.

"Automatedly aligning" in the context of the invention means in particular that the alignment is performed without requiring any assistance of the user. In other words, the automated alignment is considered as a self alignment and/or autonomous alignment of the stand and/or the microscope. The automated mechanical balancing may occur while and/or after the user moves the microscope to the user determined position.

The controllable positioning means and/or the controllable orienting means are to be understood such that the positioning means and/or the orienting means are actively controllable. For instance, the positioning means and/or the orienting means may be motorized. Preferably, the positioning means and/or the orienting means comprise one or more linkages, which may connect two or more segments of the stand in a controllably variable position and/or orientation to each other. The linkages may for instance comprise a joint connecting two segments and/or may be motorized to move the two segments along the at least one degree of freedom provided by the joint. For instance, the controllable positioning means may be configured to vary the position of the microscope with respect to the stand and/or the orienting means may be configured to vary the orientation of the microscope with respect to the object. However, when changing the position of the microscope by means of the positioning means, optionally also the orientation of the microscope with respect to the object may change. Similarly, when changing the orientation of the microscope by means of the orienting means, optionally also the position of the microscope, which may be the position of the center of mass of the microscope, may change with respect to the object. The stand and/or the controllable positioning means and/or the controllable orienting means optionally comprise at least one brake allowing to block a movement of the stand and/or the microscope with respect to the respective linkage and/or joint. For instance, such a brake may be configured to increase the friction of a movement around the respective linkage when blocking the linkage, such that no movement is possible or a movement is only possible in response to a strong force.

The target point preferably is a point in space, which is chosen to be a point of interest, i.e. a point to be observed or examined via the microscope. However, the target point may also have larger or smaller extensions than the focus point of the microscope. In particular, the target point may for instance refer to a whole region of interest, which may cover an area being larger or smaller than the field of view of the microscope when focused to a focus point within the region of interest. Preferably, the target point is a point in space, to which the microscope is aligned and/or focused or may be desired to be aligned and/or focused. The target point may be defined in a base coordinate system, which is stationary with respect to a base of the stand, such that the base of the stand and preferably the object do not move with respect to the base coordinate system at least during the alignment of the stand. However, the target point may be transformed alternatively or additionally into one or more different coordinate systems, such as one or more coordinate systems related to the linkages of the positioning means and/or the controllable orienting means. For instance, a Denavit-Hartenberg transformation may be used to transform the coordinate of the target point provided in the base coordinate system into a coordinate system related to the linkages of the stand allowing an appropriate configuration of the linkages. When using a Denavit-Hartenberg transformation, information about an angular position and/or a linear displacement of each of the linkages or joints of the stand may be required for calculating parameters needed for the transformation. For this purpose, for instance a rotary position sensor may be provided at each of the linkages for determining the angular position of the respective linkage or joint. Furthermore, for instance a linear position encoder may be provided at each segment between two adjacent linkages or joints for determining a displacement position parameter of the respective segment. For instance, a linear position decoder may be provided at each of an A-balancing slide, a B-balancing slide and/or a C-balancing slide of a stand (see for instance FIGS. 5A to 5D). The rotary position sensors and/or the linear position decoders may be connected and/or in communication with the control unit, such that the control unit may be provided with information about the rotary positions and/or linear positions. Preferably, the rotary position sensors and/or the linear position encoders may be connected to and/or integrated into the controllable positioning means and/or the controllable orienting means.

The invention provides the advantage that the position of the microscope may be changed to a different position within the accessible range of the stand by changing the configuration and/or orientation of the stand supporting the microscope, wherein the invention is able to carry out an automated realignment of the microscope to the defined target point. The microscope and/or the stand may be stabilized in the new position. In other words, the invention is capable of performing a re-orientation of the microscope in the new position to be aligned again to the previously defined target point. This allows a user, such as a surgeon, to bring the microscope to a different position with respect to the object, for instance by manually moving the microscope, e.g. to an assistant's position or to a more convenient position, and to obtain an automated realignment of the microscope to the target point from the new position chosen by the user. Thus, preferably the microscope is arranged by the user at the user determined position. Hence, the user may bring the microscope to a position, which may be ergonomically advantageous and/or may allow him to observe the object at the target point from a different view angle, without requiring him to manually realign the microscope and/or the stand manually and/or without balancing the microscope manually.

Hence, the invention particularly provides advantages regarding the ease of use of the stand and the microscope attached thereto, and also increases the freedom of the user or operator with respect to the movability of the microscope during its operation. Furthermore, the invention provides the advantage that the user is not required to take care of the realignment procedure, since the realignment to the target point can be carried out in an automated manner. Therefore, the invention allows a time-saving use of the microscope, which may be beneficial in particular during time-critical surgeries.

The realignment may be based on tracking a change of the coordinates when the user moves the microscope to a new position and/or orientation. Thus, it can be automatedly determined, by which amount every coordinate has been changed.

Based on this information, for instance a transformation can be carried out in order to determine suitable adjustments to the stand and/or linkages by means of the controllable positioning means and/or the controllable orienting means to realign the microscope to the target point from the new position chosen by the user.

Preferably, adjusting the orientation of the microscope to the target point in step c) comprises orienting the microscope such that the target point is located along the optical axis of the microscope. This allows a facilitated and/or an automated re-focusing of the microscope to the target point. Further, this allows observing the target point at a different view angle.

Preferably, adjusting the orientation of the microscope to the target point in step c) further comprises adjusting a focus parameter of the microscope to focus the microscope to the target point. This allows an automated refocusing of the microscope to the target point. For instance, the at least one focus parameter may be adjusted by changing at least one focal length and/or a position of at least one optical element, such as a lens comprised by the microscope. Thus, preferably, the microscope assembly is further configured to automatedly control a focusing parameter of the microscope.

Preferably, the steps b) and c) are carried out at least partially simultaneously and/or step b) is carried out before step c) and/or step c) is carried out before step b). In other words, the mechanical balancing may be carried out at least partly before and/or after and/or simultaneously to the automated adjusting of the orientation. More preferably, the steps b) and c) may be carried out in an open loop and/or in a closed loop, which may be advantageous for controlling and/or stabilizing the focus at the target point.

Preferably, stabilizing the microscope in step b) comprises mechanically and optionally automatedly balancing the microscope by adjusting the controllable positioning means and/or the controllable orienting means such that the microscope rests at the user determined position. Mechanically balancing preferably means that the stand is adjusted such that the microscope does not change its position and orientation, if not actively moved, for instance by the user and/or the controllable orienting means and/or the controllable positioning means. More preferably, mechanically balancing means that the microscope does not change the position of its center of mass, in particular due to gravitational force, if not actively used by external forces. Alternatively or additionally to mechanically balancing the microscope, the step of stabilizing the microscope may comprise blocking at least a part of linkages of the controllable positioning means and/or the controllable orienting means, for instance by means of brakes provided at the respective linkages, which may block a movements around the respective joints and/or rotational axes.

Preferably, the target point is defined on the basis of a user input. This allows that the user may define the target point, to which the microscope shall be alignable in an automated manner by providing a respective input. Alternatively or additionally, the target point is defined on the basis of provided object data. The object data may be provided for instance on the basis of imaging data retrieved by other imaging techniques, such as for example MRT and/or CT and/or ultrasound and/or other conventional medical imaging techniques. For instance, a target point at the object may be chosen in CT imaging data and the stand and the microscope may be configured to subsequently position and/or orient and/or align the stand and/or the microscope to focus to the chosen target point. Alternatively and/or additionally the target point is defined by determining and saving a focus point, to which the microscope is focused when a predetermined user input is provided. For instance, a user of the microscope may save the focus point, to which the microscope is currently focused as a target point, which will allow an automatic realignment of the stand and/or the microscope to the focus point currently under investigation.

Preferably, at least the steps b) and c) are carried out automatedly in a continuous manner. In particular, the steps b) and c) may be carried out repeatedly in an automated manner. This provides the advantage that the focus of the microscope can be stabilized and aligned to the target point. For example, the user may change the position and/or the orientation of the microscope while the stabilization and/or realignment is activated and, hence, at least the steps b) and c) are carried out automatedly in a continuous manner to maintain the microscope stabilized and aligned to the target point. By this, the alignment towards the target point may be permanently maintained, despite a possible short period of time, which may be required for the realignment which may be for instance not more than 3 seconds. This mode may be regarded for instance as a dynamic realignment mode.

Alternatively or additionally, at least the steps b) and c) are carried out in response to a user input requesting a re-alignment of the microscope to the target point. In other words, according to another preferred embodiment, the stabilizing and realignment is not carried out permanently but only when requested, as for example by a respective user input. This may allow for example the possibility for the user to freely move the microscope to different positions and/or orientations and/or to observe other points of interest besides the target point without an automated realignment back to the target point, and preferably a single automated realignment back to the target point at the present position of the microscope when requested by the user. This mode may be regarded for instance as a static realignment mode.

Further advantages and embodiments of the invention will become apparent from the description and the appended figures.

It should be noted that the previously mentioned features and the features to be further described in the following are usable not only in the respectively indicated combination, but also in further combinations or taken alone, without departing from the scope of the present invention.

BRIEF DESCRIPTION OF THE DRAWING VIEWS

Figure 2:
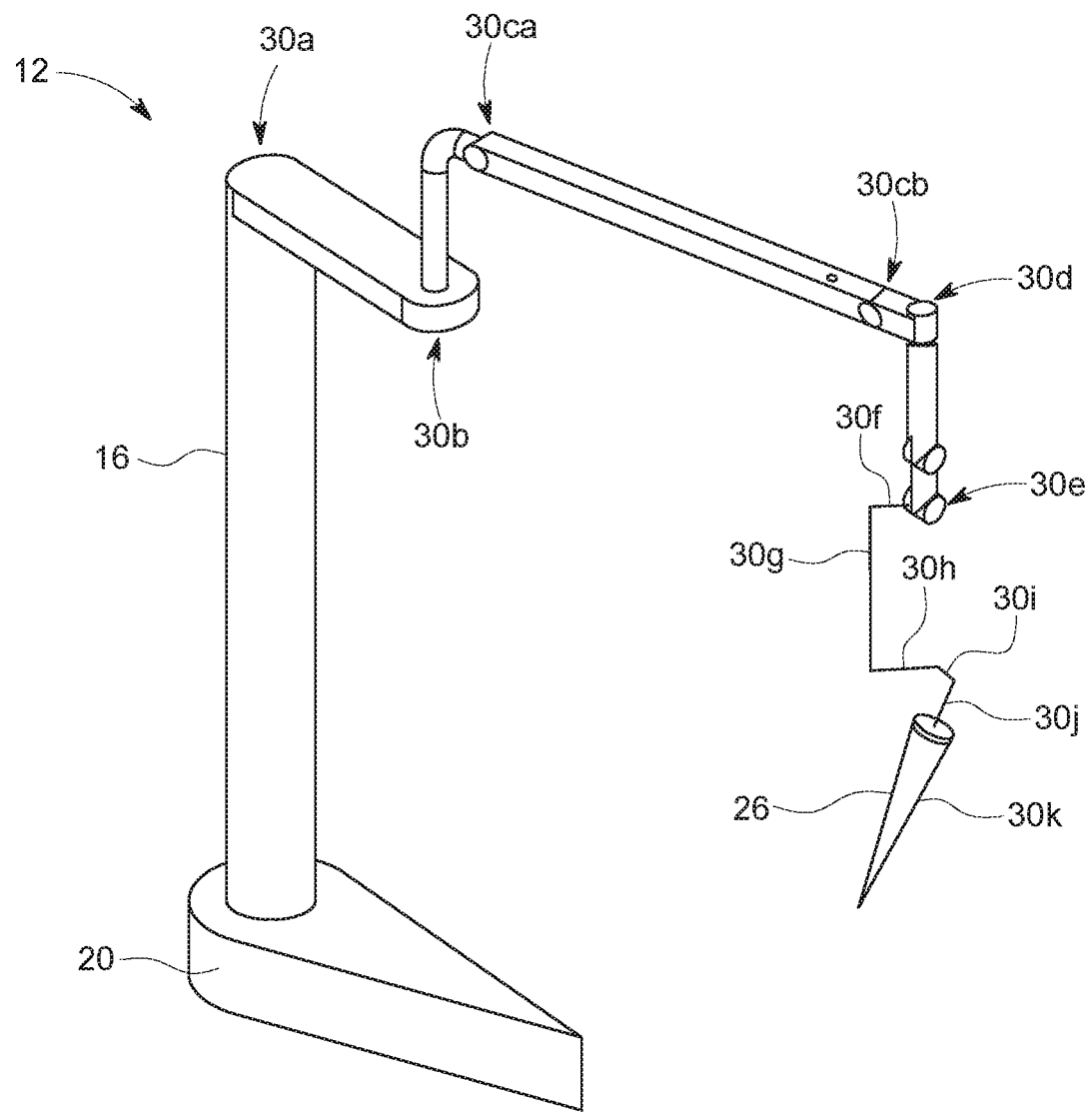
FIG. 2 depicts a stand according to a preferred embodiment.
Figure 3A:
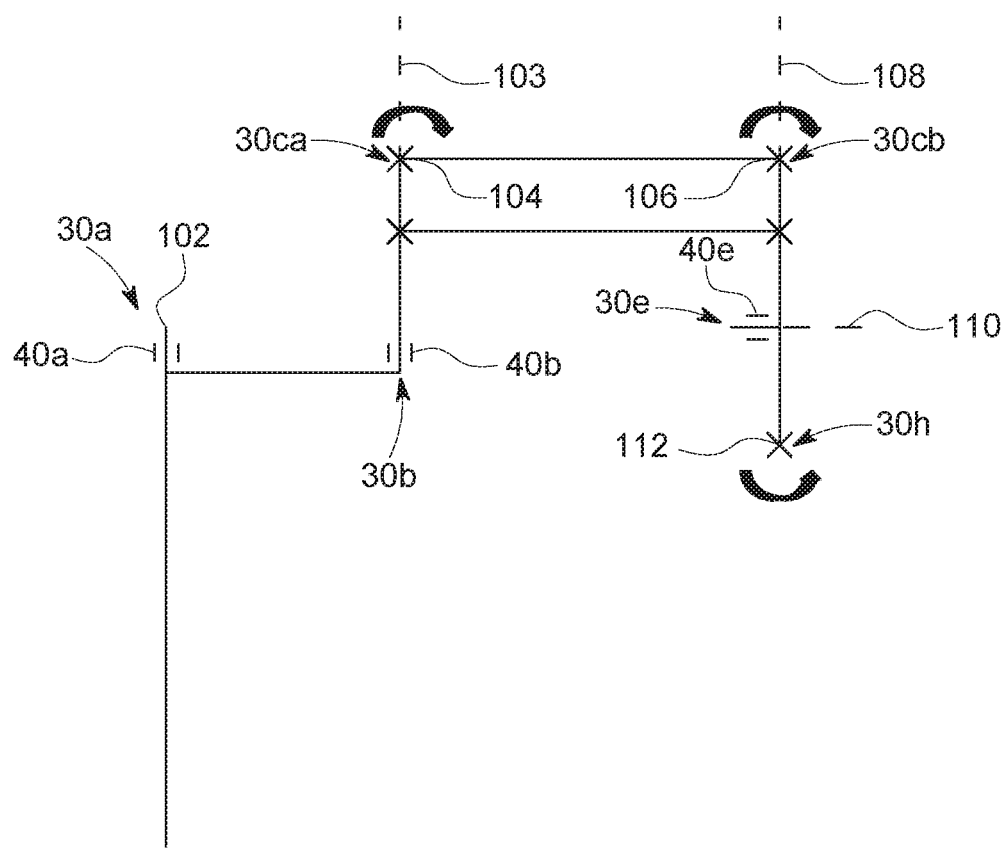
Figure 3B:
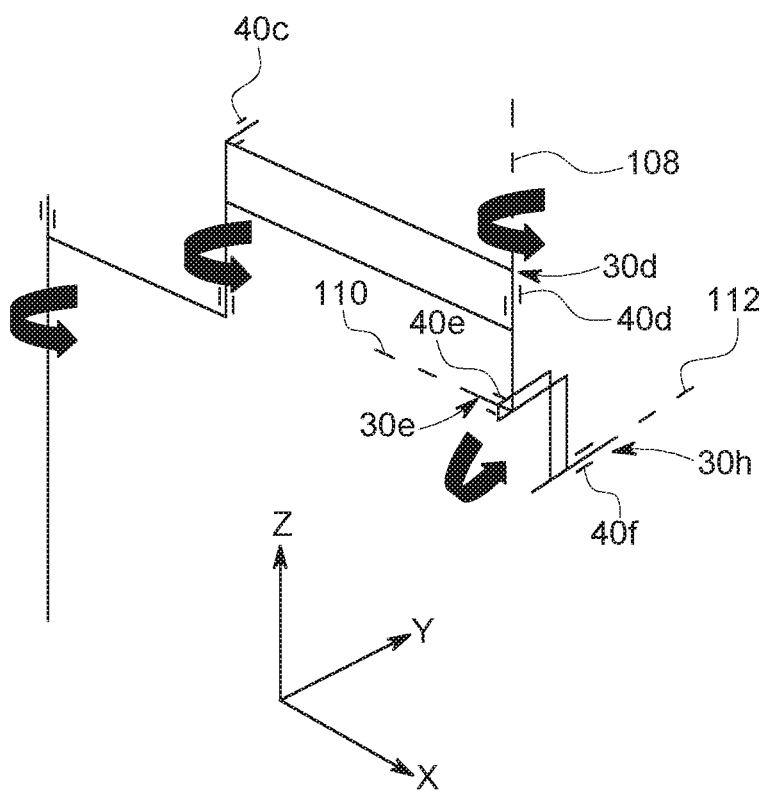

FIGS. 3A and 3B give a schematic overview from different viewing perspectives over the linkages of the stand shown in FIG. 2.

Figure 4:
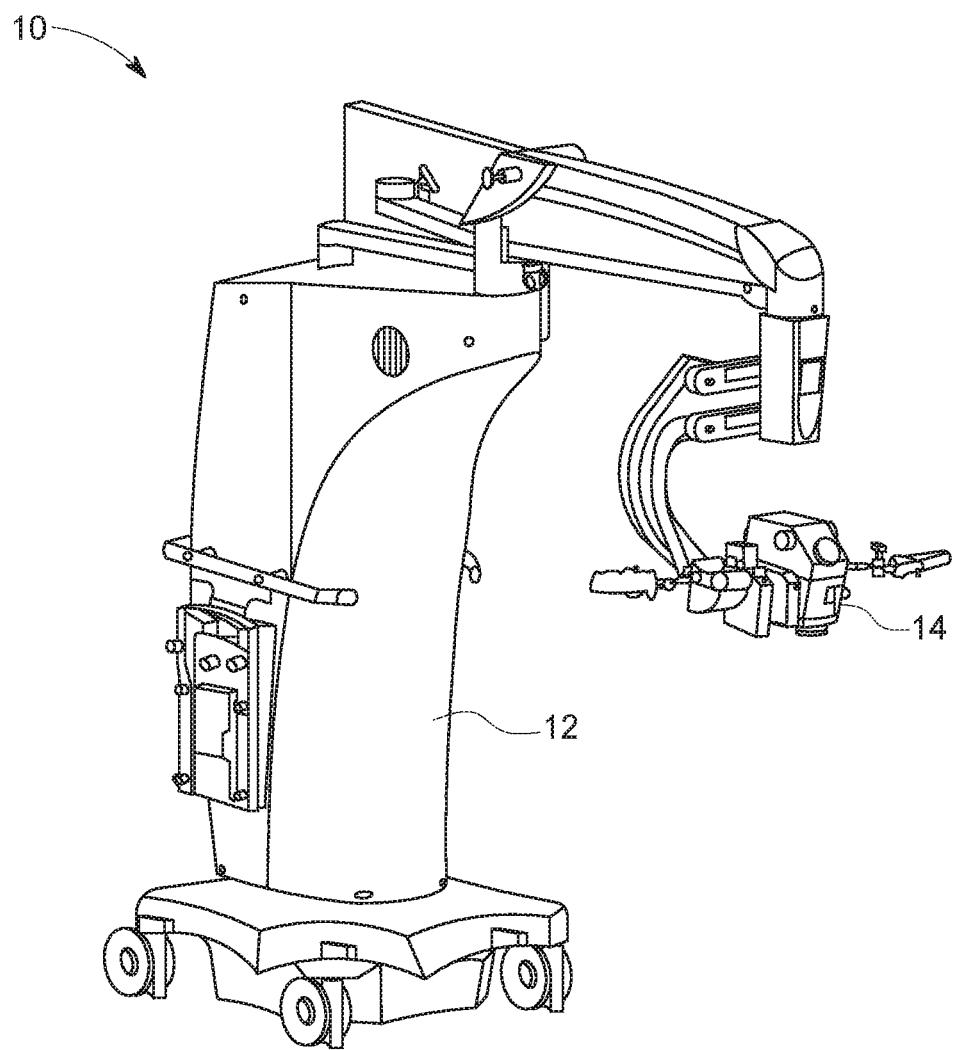

FIG. 4 shows a microscope assembly according to another preferred embodiment.

FIGS. 5A to 5D show a stand according to a preferred embodiment comprising balancing means for balancing the microscope around several rotational axes.

DETAILED DESCRIPTION OF THE INVENTION

Figure 1A:
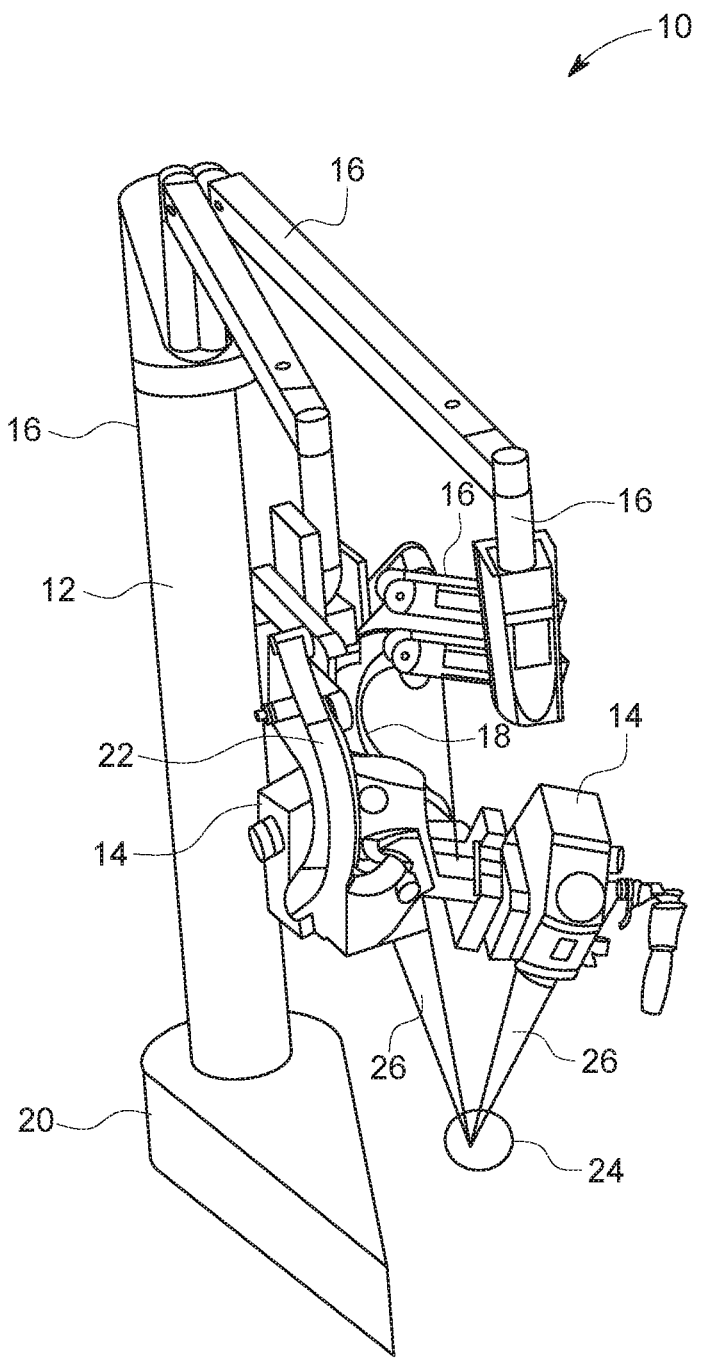
FIGS. 1A and 1B depict a microscope assembly according to a preferred embodiment.
Figure 1B:
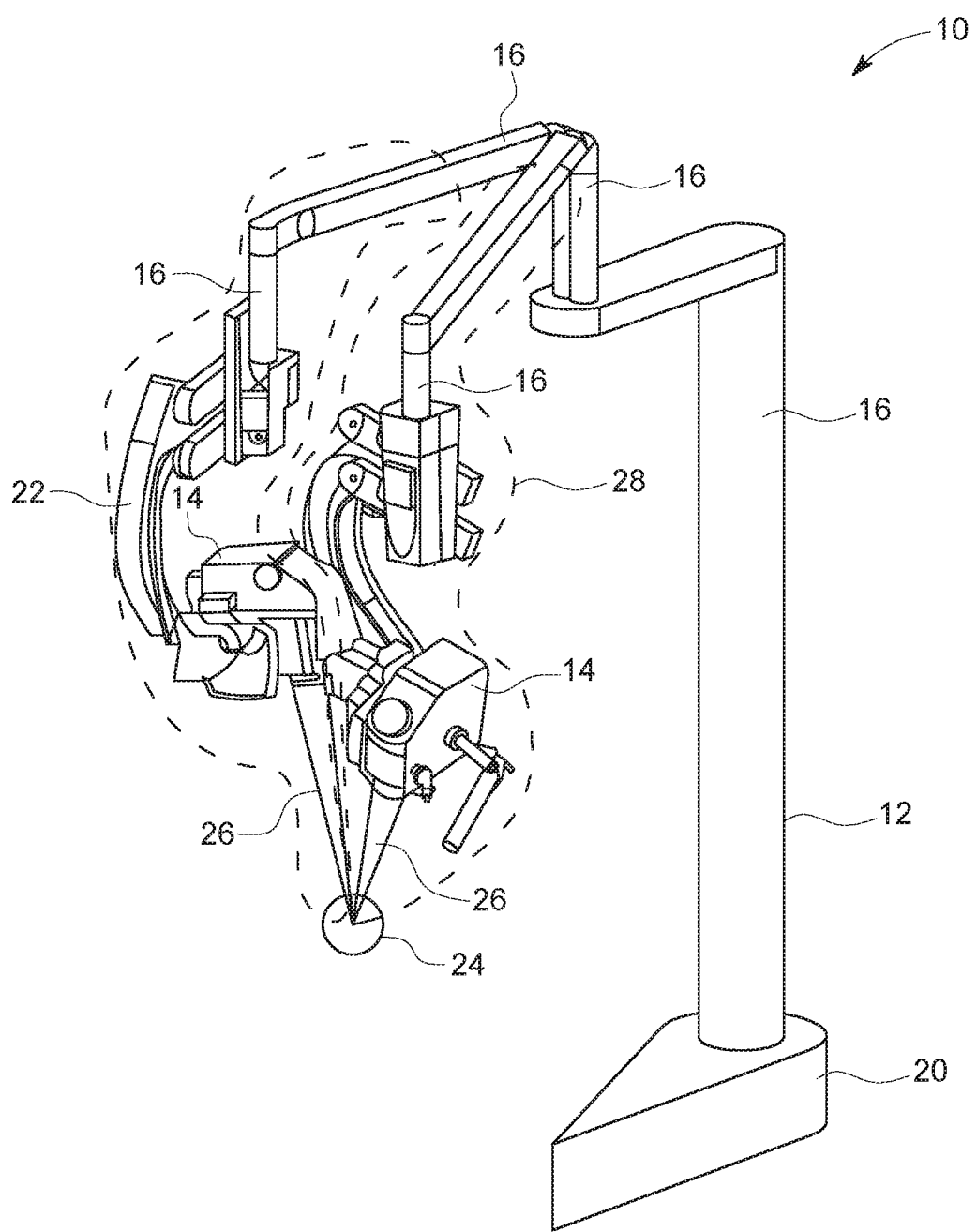

FIGS. 1A and 1B depict a microscope assembly 10 according to a preferred embodiment comprising a stand 12 and a microscope 14, wherein the microscope 14 is attached to and supported by the stand 12. The microscope 14 is supported by the stand 12 such that the microscope 14 is movable, i.e. the position and/or orientation of the microscope 14 may be changed by a respective reconfiguration of the stand 12, within a certain range defined by the stand 12. In particular, FIGS. 1A and 1B each show the microscope 14 positioned and oriented in two different positions and orientations. Thus, although FIGS. 1A and 1B each show two microscopes 14, only one microscope 14 is attached to the stand 12 but is for better illustration shown in two different positions and orientations.

The stand 12a comprises controllable positioning means 16 and controllable orienting means 18 for positioning and/or orienting the microscope 14 with respect to an object (not shown), which is preferably arranged in a stationary manner with respect to a base 20 of the stand 12. For instance, the object may be arranged and/or attached to an object table (not shown), wherein the object table and the base 20 of the stand 12 are preferably attached to a solid support, such as a ground, to prevent relative movements between the object and the base 20 of the stand 12 and the object.

By moving and/or rearranging and/or reconfiguring the controllable positioning means 16 and the controllable orienting means 18, the microscope 14 can be brought into and stabilized at different positions and/or orientations. Preferably, when arranged and stabilized at a specific position by the stand 12, the microscope 14 preferably does not move itself, for instance due to a gravitational force, because the microscope may be balanced and/or a respective movement may be blocked. Furthermore, if no movement of the microscope 14 is required, for example if a movement of the microscope 14 by the user and/or by the stand 12 are not intended, the controllable positioning means 16 and controllable orienting means 18 may preferably block a movement of the microscope 14 to prevent any unintentional movement of the microscope 14 and/or the stand 12 with respect to the object. For instance, in a preferred embodiment it is necessary to unlock and/or unblock the stand 12 and/or the microscope 14 to allow the user moving the microscope 14. This may be done by locking and/or releasing at least one brake provided in the stand.

The controllable positioning means 16 and/or the controllable orienting means 18 comprise arms and/or levers and/or telescopic arms and/or linkages, such as joints and/or hinges, providing a large flexibility of the stand 12 regarding movements in all three spatial positional and rotatory degrees of freedom. Furthermore, the controllable positioning means 16 and/or controllable orienting means 18 comprise a C-Slide 22 for accurately and/or conveniently, mechanically balancing the microscope 14.

In particular the stand 12 allows the microscope 14 to be brought to different positions and to orient the microscope 14 in each of the different positions in a suitable manner to allow the microscope 14 to focus onto a predetermined target point 24. The target point 24 is highlighted by a circle 25, which surrounds a region of interest, which may represent or comprise the target point 24. As can be seen in FIGS. 1A and 1B from different perspectives, at both positions and in both orientations the microscope 14 is aligned towards the target point 24 and can be focused to the target point 24. The light cones 26 exemplary indicate the light rays emerging from the target point 24, which may be collected by the objective lens of the microscope 14. Moreover, from FIGS. 1A and 1B it is evident that the microscope assembly 10 allows a user to observe the target point 24 from different viewing angles and/or different point of views. Alternatively or additionally, a user may bring the microscope 14 from one position to the other position for example for handling the microscope in an ergonomically more convenient manner, wherein the microscope 14 can be realigned to the target point 24 at the new position automatically or when requested by the user by means of a respective user input.

As already mentioned, FIG. 1B shows the same preferred embodiment as FIG. 1A from a different perspective. In addition, the dashed lines 28 shown in FIG. 1B highlight the components of the microscope assembly 10 represented in the two different positions and orientations.

FIG. 2 depicts a stand 12 according to a preferred embodiment showing the available linkages 30a to 30k of the controllable positioning means 16 and the controllable orienting means 18 in detail. The stand 12 may be motorized to automatedly move the stand with respect to the linkages 30a to 30k.

By means of the linkages 30a to 30k the microscope 14 may be positioned and/or oriented with respect to the object and/or balanced. The linkage 30k depicts the light cone 26, which means that according to a preferred embodiment also at least one focusing parameter of the microscope may be modified and be treated as a linkage, allowing to automatedly focus the microscope to the target point 24. At least some of the linkages, preferably all linkages, may be equipped with at least one brake allowing to block movements with respect to the respective linkage.

FIGS. 3A and 3B give a schematic overview from different viewing perspectives over the linkages of the stand 12 shown in FIG. 2. The linkages 30a to 30h are shown in combination with the axes 102 to 112, around which the respective linkages are configured to be moved or turned. In addition, braking elements 40a to 40f are depicted, which may be used to brake down a movement of the stand 12 or one or more of its segments around the associated axis or to lock or block a respective movement. By means of linkage 30a the stand may be turned or rotated around axis 102. The linkage 30b allows rotating the stand 12 around axis 103. The linkages 30ca and 30cb allow rotating the stand 12 around the axes 104 and 106. Linkage 30d allows rotating the stand 12 around axis 108. Further, by means of linkage 40e the stand 12 may be rotated around axis 110 and by means of linkage 30h the stand 12 may be rotated around linkage 30h. That the stand 12 may be rotated and/or turned and/or moved around a specific axis does not necessarily mean that the whole stand 12 must be swingable and/or turnable and/or movable around this axis, but is also satisfied when only certain parts and/or linkages of the stand are swingable and/or turnable and/or movable around this axis. In addition, FIG. 3B shows an exemplary base coordinate system 200, which may be used for navigation and/or orientation and/or positioning with respect to the object and/or the base coordinate system. For instance, the target point may be selected and/or provided in the base coordinate system.

In the following, an exemplary method according to a preferred embodiment for automatedly aligning a stand for a microscope is presented, without limiting the invention to this specific embodiment.

In a first step, base coordinate system is set up as a reference coordinate system, which may be represented by a x-, y- and z-axis as shown in coordinate system 200 in FIG. 3B. The maximum movable range and/or the zero positions of all linkages may be defined in all dimensions of the based coordinate system. In particular, a target point is defined or locked in the base coordinate system.

In a second step, a transformation is performed, such as a Denavit-Hartenberg transformation or the like, to the desired coordinates of the target point to be locked from the base coordinate system into the linkage coordinate system. Three-dimensional, homogeneous transformations are carried out for the parameters of the subsequent linkages starting from the base 20 of the stand 12 towards the target point 24 covering all linkages 30a to 30k, which are necessary to position and/or orient the microscope 14 appropriately. This may require a large number of transformations, which may depend on the number of linkages in the system or on the number of linkages required to align the microscope to the target point. In particular, one variable may be required per linkage, as shown in FIGS. 3A and 3B, wherein the movements of the linkages may comprise rotational movements and/or linear translations. When the desired parameters or coordinates have been found which result in the microscope 14 to be aligned towards the target point 24, the parameters or coordinates are saved. For the Denavit-Hartenberg transformation, information about an angular position and/or a linear displacement of each of the linkages or joints of the stand may be required for calculating parameters needed for the transformation. For this purpose, for instance a rotary position sensor may be provided at each of the linkages for determining the angular position of the respective linkage or joint. Furthermore, for instance a linear position encoder may be provided at each segment between two adjacent linkages or joints for determining a displacement position parameter of the respective segment. For instance, a linear position decoder may be provided at each of an A-balancing slide, a B-balancing slide and/or a C-balancing slide of a stand (see for instance FIGS. 5A to 5D). The rotary position sensors and/or the linear position decoders may be connected and/or in communication with the control unit. Preferably, the rotary position sensors and/or the linear position encoders may be connected to and/or integrated into the controllable positioning means and/or the controllable orienting means.

In a third step, the user or operator of the microscope 14 is free to move/change all the variables, i.e. all the parameters or settings of the linkages to a new position. From the new position/s, three-dimensional homogeneous transformations are done again to the point of Axis 108. The parameter for setting the linkage 30d at Axis 108 shall be calculated such that the microscope shall be aligned towards the target point 24 with new C-slide position (due to balancing) and x-axis horizontal (angle: 0°). The C-slide position may be represented by linkage 30e and the x-axis by axis 110.

A preferred embodiment of a stand 12 with several balancing devices is illustrated with reference to FIGS. 5A to 5D further below, illustrating the various slides and axis of the stand and the microscope.

In a fourth step, the calculation of the parameter of axis 108 is calculated such that the required rotation angle for turning the microscope 14 from the current orientation and position towards the target point 24 is minimized. Preferably, the calculation is carried out such that at least 90° of rotational movement to the left and/or to the right remain available after setting the parameter to linkage 30d.

In a fifth step, the calculated parameter, i.e. the angle to be set, for linkage 30d and axis 108 angle is calculated in subsequent three-dimensional homogeneous transformations and it is checked that the microscope is horizontally aligned with respect to axis 110. Afterwards, the desired y-axis angle with respect to axis 112 is calculated to ensure that the microscope 14 is aligned towards the target point 24. The calculation may account for two possible cases, in which the tilt direction (with respect to axis 112) will be either above horizontal orientation (angle>90°) or below horizontal orientation. Other possibilities can also be made to avoid the optics carrier from tilting towards user (angle<0°), which means that the optical axis may be tilted towards the user of the microscope.

In a sixth step the working distance required from objective lens interface to the target point is calculated. If the required parameters are out of range of the linkages and/or out of the optical capability of the microscope, a feedback may be provided to the user to inform the user that the chosen position and/or orientation might not be suitable for observing the target point.

In a seventh step, the above-discussed steps 1 to 6 may be applied in a static or dynamic realignment mode. For the dynamic mode, the system shall propose to remain in situ upon leaving an "in-range" kinematic region. For the dynamic mode, the control methodology and system hardware (e.g. motor speed and mechanical advantage) should be provided in a suitable manner to minimize delay the delay, i.e. to be provided with sufficient computational power.

For instance, the linkages 30a to 30cb may be regarded as the controllable positioning means 16 and the linkages 30d to 30k may be regarded as the controllable orienting means 18 of the stand 12.

FIG. 4 shows a microscope assembly 10 according to another preferred embodiment. According to this embodiment, the microscope assembly 10 may be in principle movable, i.e. the base of the assembly 10 is movable. This allows installing the microscope assembly 10 at a surgical table if needed and to remove it otherwise. However, for performing an automated aligning of the stand 12 for the microscope to a target point, which may be defined and stationary with respect to the surgical table, it is most preferred that the microscope assembly 10 is not moved relative to the target point 24, i.e. with respect to the surgical table, while the method for automatedly aligning the stand 12 for the microscope 14 is still operating.

Figure 5A:
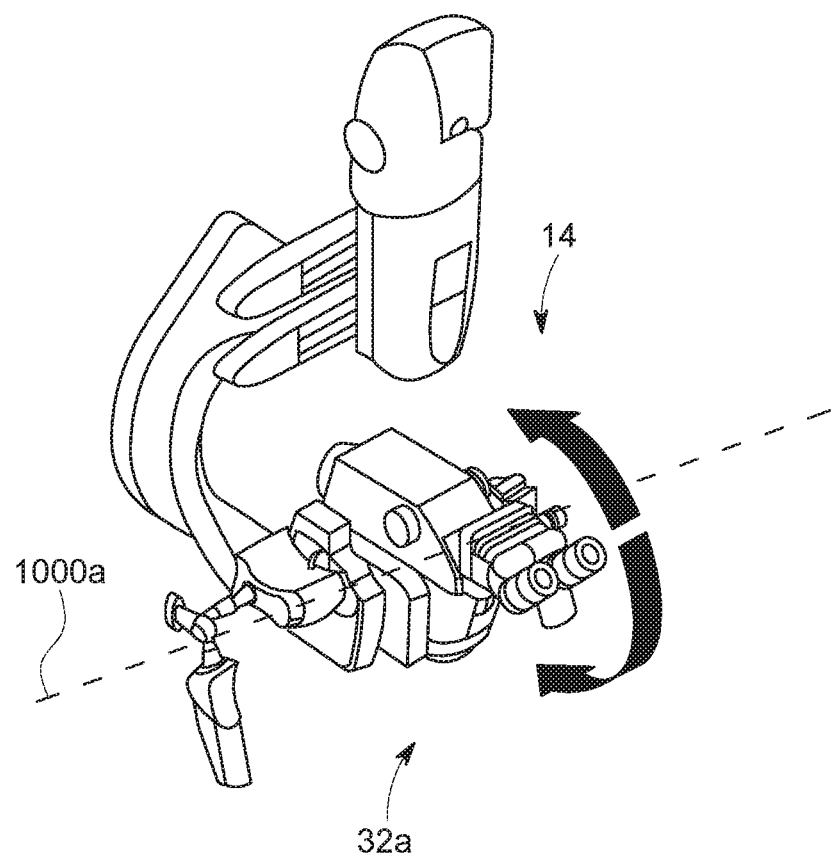
Figure 5B:
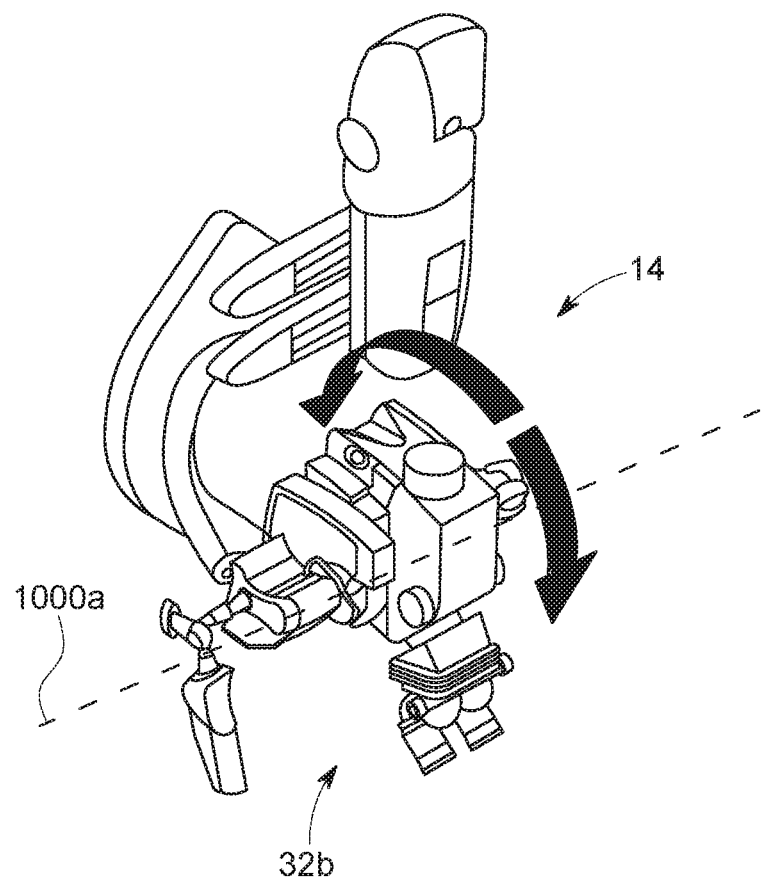
Figure 5C:
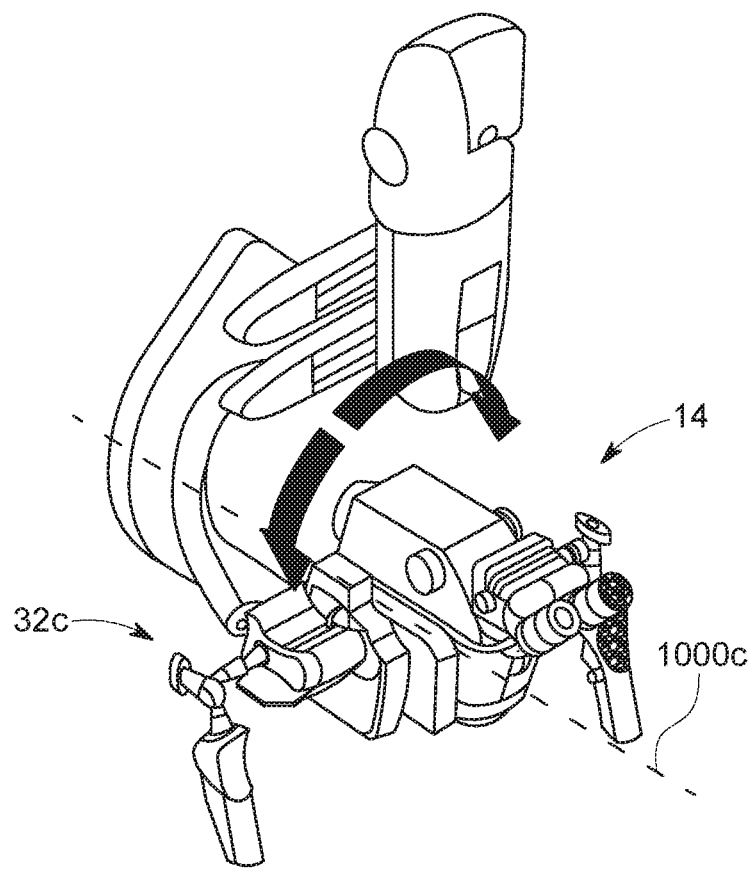
Figure 5D:
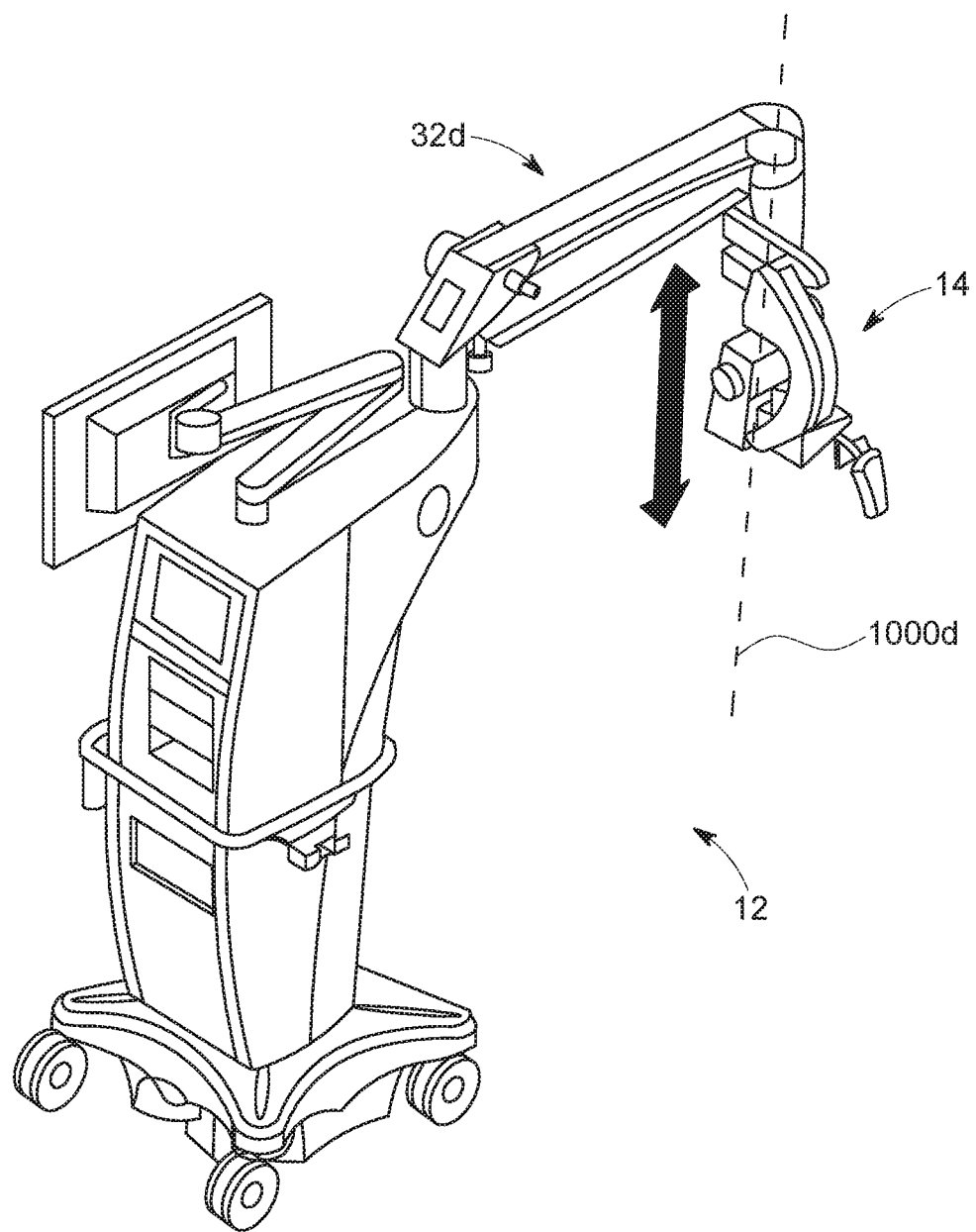

FIGS. 5A to 5D illustrate an exemplary stand 12 supporting a microscope 14, wherein the stand 12 comprises several balancing devices 32, each for balancing the microscope 14 with respect to a specific rotation axis. FIG. 5A indicates a balancing device 32a for balancing the microscope with respect to the rotation axis 1000a, wherein the balancing device 32a is configured as an A-balancing slide. FIG. 5B shows a balancing device 32b configured as a B-balancing slide, which is also adapted to balance the microscope 14 around the rotation axis 1000a in a different orientation. The balancing devices 32a and 32b, i.e. the A-balancing slide and the B-balancing slide, may form together an AB-balancing unit. FIG. 5C illustrates a balancing device 32c for balancing the microscope 14 around a rotation axis 1000c, wherein the balancing device 32c may be adapted as a C-balancing device. FIG. 5D depicts a whole stand 12 and in particular a balancing device 32d for balancing the microscope 14 and the stand 12 along a D-axis 1000d, wherein the balancing device 32d is adapted as a D-balancing device.

LIST OF REFERENCE SIGNS 10 microscope assembly
12 stand
14 microscope
16 positioning means
18 orienting means
20 base (of the stand)
22 C-slide
24 circle/target point
26 light cone
28 dashed line indicating the components of the microscope assembly
30a-30k linkage
32 balancing device
102-112 axes
200 base coordinate system

What is claimed is:

1. A method for automatedly aligning a stand for a microscope, wherein the stand comprises a controllable positioning means for positioning the microscope and a controllable orienting means for orienting the microscope, the method comprising the steps of:
  a) defining a target point to be observed by the microscope, wherein the target point is located within a coordinate range accessible by the stand;
  b) stabilizing the microscope at a user determined position in an automated manner using the controllable positioning means of the stand; and
  c) adjusting an orientation of the microscope at the user determined position to the defined target point in an automated manner using the controllable orienting means of the stand;
  wherein the target point is defined in a control unit for the controllable positioning means, before steps b) and c) are performed, on the basis of a user input and/or on the basis of provided object data and/or by determining and saving a focus point to which the microscope is focused when a predetermined user input is provided.

2. The method according to claim 1, wherein adjusting the orientation of the microscope to the target point in the step c) comprises orienting the microscope such that the target point is located along an optical axis of the microscope.

3. The method according to claim 2, wherein adjusting the orientation of the microscope to the target point in step c) further comprises adjusting a focus parameter of the microscope to focus the microscope to the target point.

4. The method according to claim 1, wherein the steps b) and c) are carried out at least partially simultaneously.

5. The method according to claim 1, wherein the step b) is carried out before the step c).

6. The method according to claim 1, wherein the step c) is carried out before the step b).

7. The method according to claim 1, wherein the controllable positioning means and the controllable orienting means collectively comprise a plurality of linkages, and wherein stabilizing the microscope in the step b) comprises
  mechanically balancing the microscope by adjusting at least one of the controllable positioning means and/or the controllable orienting means such that the microscope rests at the user determined position; and/or
  blocking at least one of the plurality of linkages.

8. The method according to claim 1, wherein the microscope is arranged by the user at the user determined position.

9. The method according claim 1, wherein at least the steps b) and c) are carried out automatedly in a continuous manner.

10. The method according to claim 1, wherein at least the steps b) and c) are carried out in response to a user input requesting a re-alignment of the microscope to the target point.

11. A control unit for a stand for a microscope, wherein the control unit is configured to cause the stand to carry out the method according to claim 1.

12. A computer-readable data storage medium having a computer program stored thereon, wherein the computer program is configured such that execution of the computer program by a control unit of a stand for a microscope causes the stand to carry out the method according to claim 1.

13. A stand for a microscope for automatedly aligning the microscope to a target point, the stand comprising:
  controllable positioning means for positioning the microscope with respect to an object to be observed with the microscope;
  controllable orienting means for orienting the microscope with respect to the object; and
  a control unit configured to:
  a) define a target point to be observed by the microscope, wherein the target point is located within a coordinate range accessible by the stand;
  b) stabilize the microscope at a user determined position in an automated manner using the controllable positioning means of the stand; and
  c) adjust an orientation of the microscope at the user determined position to the target point in an automated manner using the controllable orienting means of the stand;
  wherein the target point is defined in the control unit before steps b) and c) are performed, on the basis of a user input and/or on the basis of provided object data and/or by determining and saving a focus point to which the microscope is focused when a predetermined user input is provided.

14. The stand according to claim 13, wherein the control unit is further configured to adjust a focus parameter of the microscope to focus the microscope to the target point.

15. A microscope assembly comprising a stand according to claim 13 and a microscope attached to the stand.

16. The microscope assembly according to claim 15, wherein the microscope assembly is configured to automatedly control a focusing parameter of the microscope.

* * * * *